(12) United States Patent
Kirschman

(10) Patent No.: US 8,998,906 B2
(45) Date of Patent: Apr. 7, 2015

(54) SURGICAL IMPLANT INSERTER COMPRESSOR

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 196 days.

(21) Appl. No.: 13/544,311

(22) Filed: Jul. 9, 2012

(65) Prior Publication Data

US 2014/0012338 A1 Jan. 9, 2014

(51) Int. Cl.
*A61B 17/88* (2006.01)
*A61B 17/70* (2006.01)
*A61B 17/80* (2006.01)

(52) U.S. Cl.
CPC .............. *A61B 17/808* (2013.01); *A61B 17/70* (2013.01); *A61B 17/7068* (2013.01); *A61B 17/8872* (2013.01)

(58) Field of Classification Search
USPC .................... 606/109, 99, 248–249, 205–208
See application file for complete search history.

(56) References Cited

U.S. PATENT DOCUMENTS

| | | | |
|---|---|---|---|
| 5,735,857 A | 4/1998 | Lane | |
| 6,716,218 B2 * | 4/2004 | Holmes et al. | 606/105 |
| 7,387,635 B2 | 6/2008 | Keller | |
| 7,473,254 B2 | 1/2009 | White et al. | |
| 7,476,240 B2 | 1/2009 | Raymond et al. | |
| 7,520,888 B2 | 4/2009 | Trieu | |
| 7,588,591 B2 | 9/2009 | Hartmann et al. | |
| 7,608,078 B2 | 10/2009 | Berry | |
| 7,713,274 B2 * | 5/2010 | Shluzas et al. | 606/105 |
| 7,806,901 B2 | 10/2010 | Stad et al. | |
| 8,123,807 B2 | 2/2012 | Kim | |
| 8,262,697 B2 | 9/2012 | Kirschman | |
| 8,685,065 B1 * | 4/2014 | Taber et al. | 606/279 |
| 2003/0083747 A1 | 5/2003 | Winterbottom et al. | |
| 2003/0212402 A1 | 11/2003 | White et al. | |
| 2003/0225416 A1 * | 12/2003 | Bonvallet et al. | 606/105 |
| 2005/0159757 A1 * | 7/2005 | Shluzas et al. | 606/105 |
| 2006/0142777 A1 * | 6/2006 | Bastian | 606/88 |
| 2009/0240280 A1 * | 9/2009 | Wang et al. | 606/207 |
| 2011/0022090 A1 * | 1/2011 | Gordon et al. | 606/249 |
| 2011/0172711 A1 | 7/2011 | Kirschman | |
| 2011/0224740 A1 * | 9/2011 | Smisson et al. | 606/86 A |
| 2011/0319936 A1 * | 12/2011 | Gordon et al. | 606/248 |

* cited by examiner

*Primary Examiner* — Jan Christopher Merene
(74) *Attorney, Agent, or Firm* — Jacox, Meckstroth & Jenkins

(57) ABSTRACT

A surgical implant inserter compressor is shown having a plurality of jaws and is adapted to permit at least one or both jaws to move generally parallel with respect to each other or move along an axis wherein the jaws remain in a plane that is generally perpendicular to that axis. The surgical implant inserter compressor is adapted for implanting at least one or a plurality of plates onto a pair of spinous processes and is adapted to distribute the clamping force with which the implants engage the spinous processes. The surgical implant inserter compressor may be adapted to permit one or both jaws to float or pivot to accommodate different anatomical structures, such as spinous processes that are not aligned, are of different sizes or shape and the like. An optional tool guide for guiding a tool to drive a lock to lock the plates together is also shown.

12 Claims, 7 Drawing Sheets

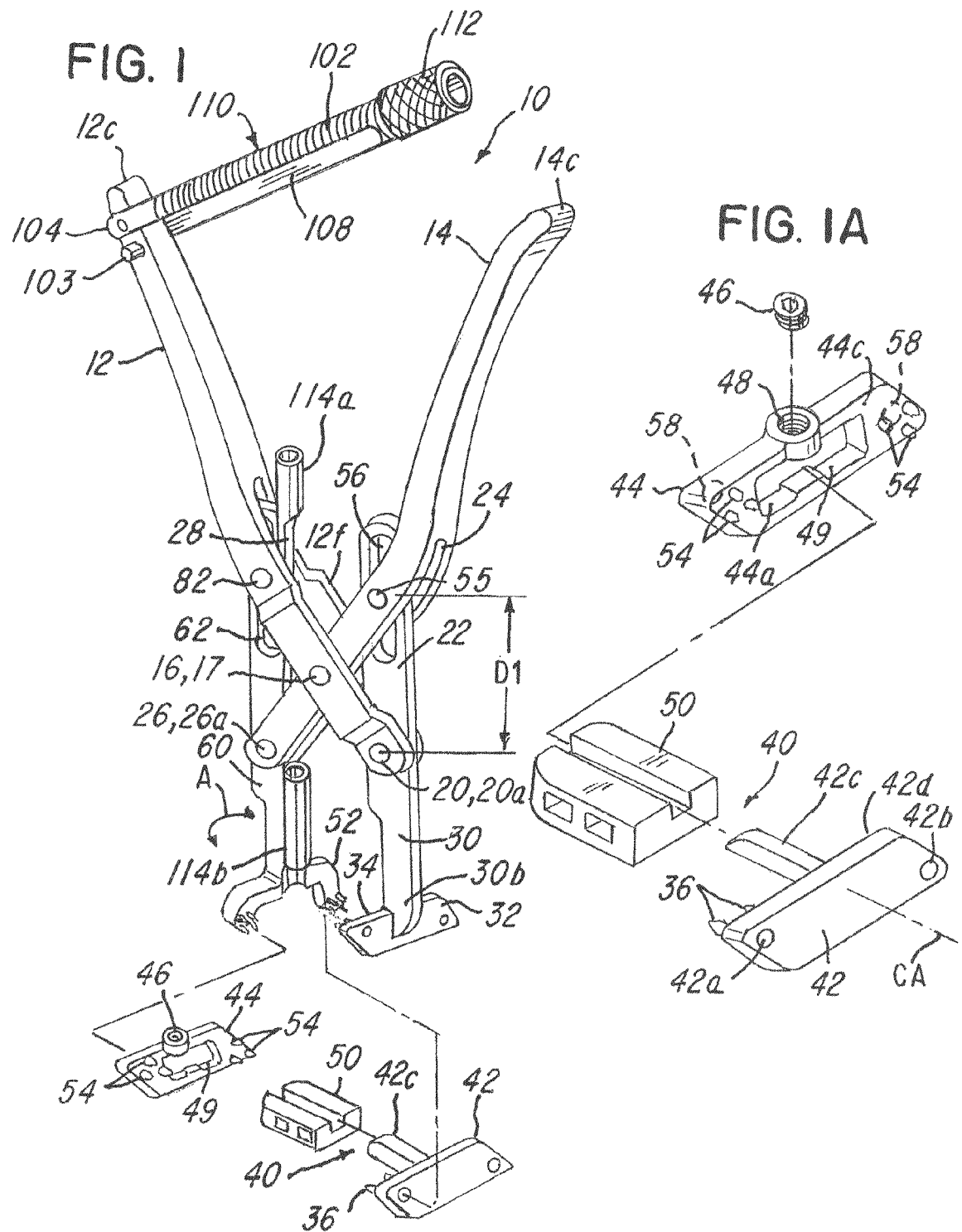

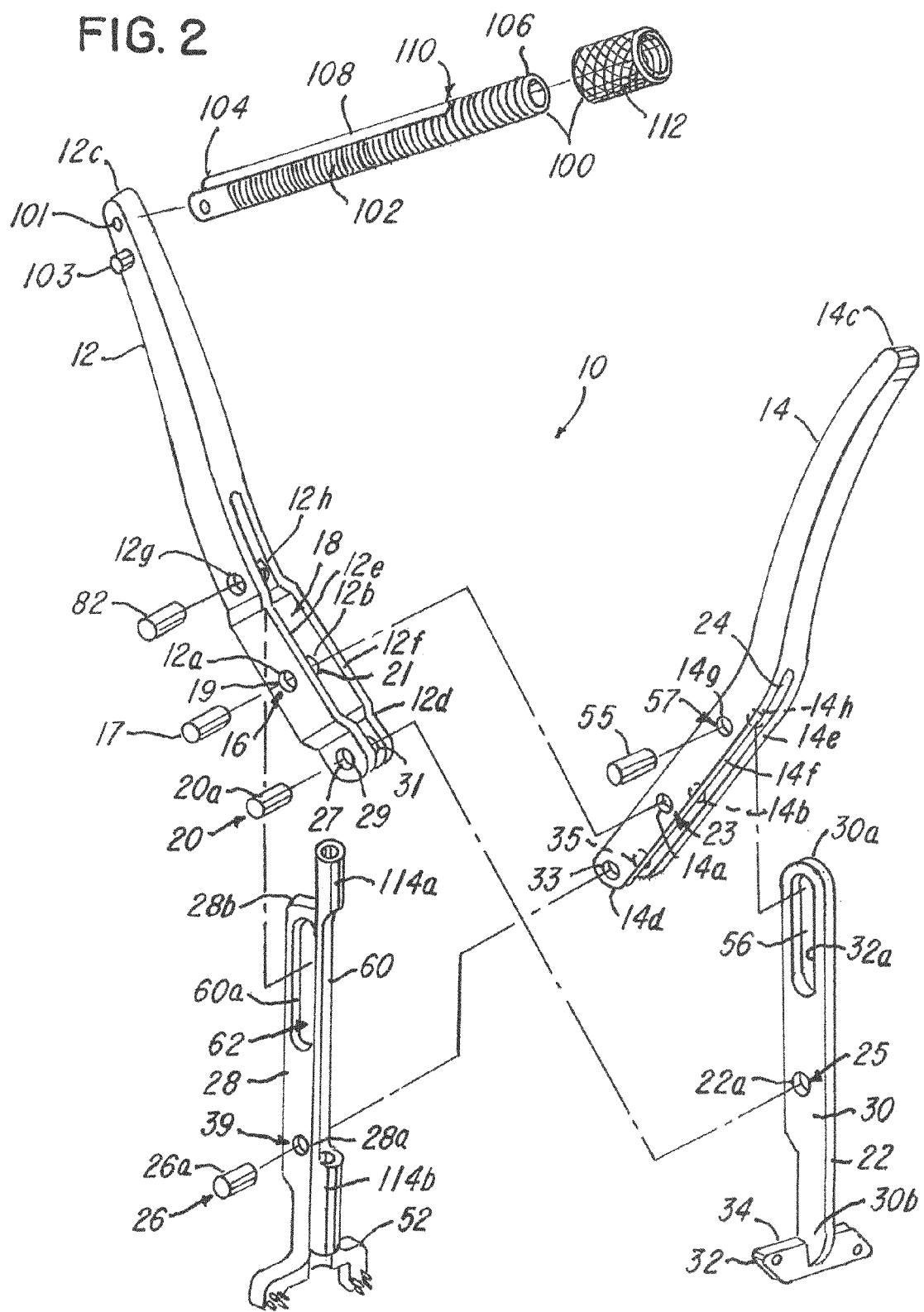

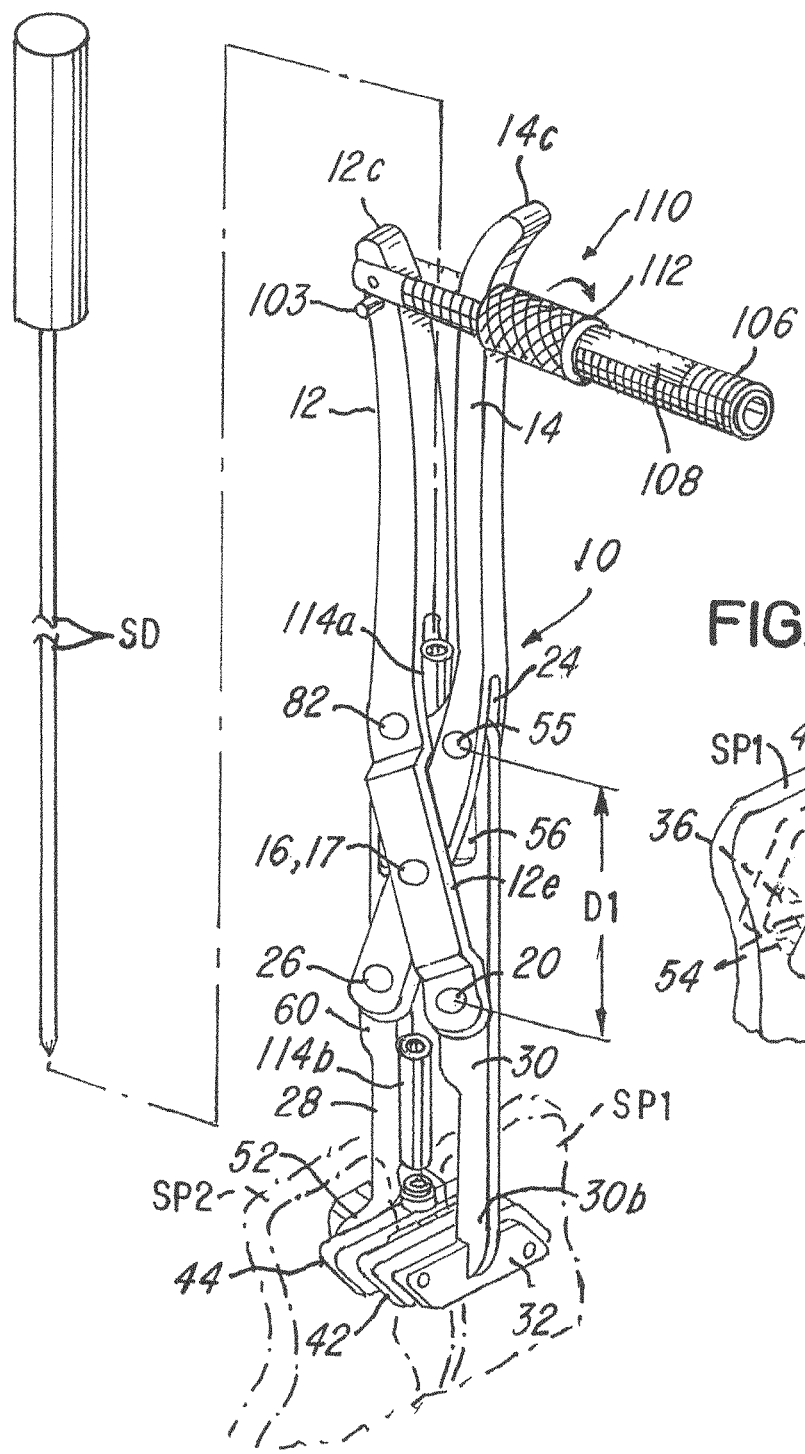
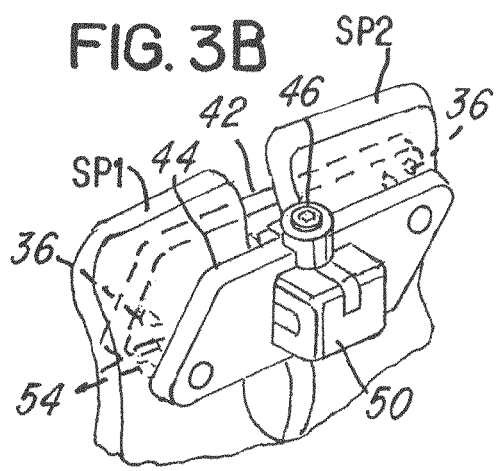
FIG. 3A
FIG. 3B

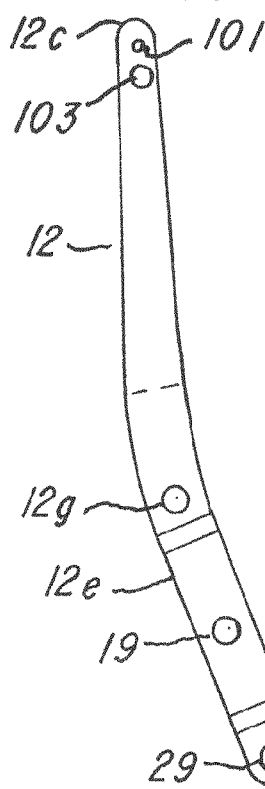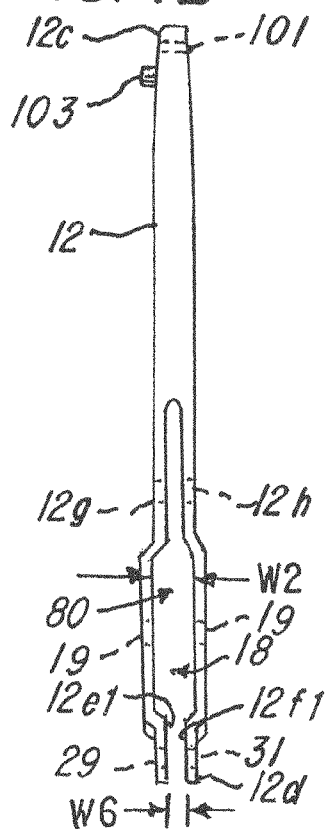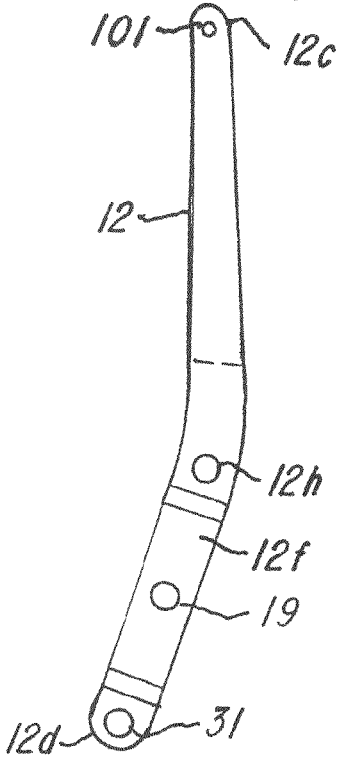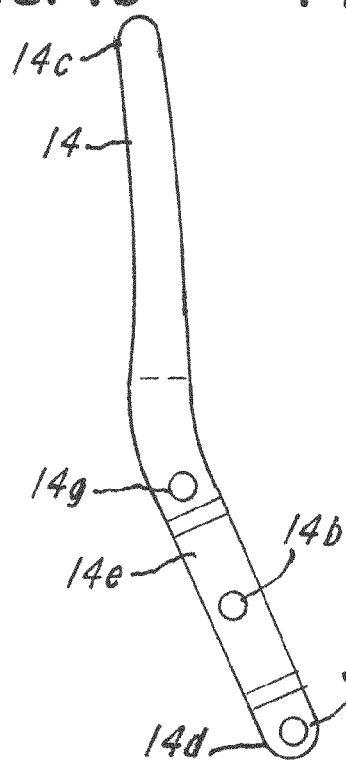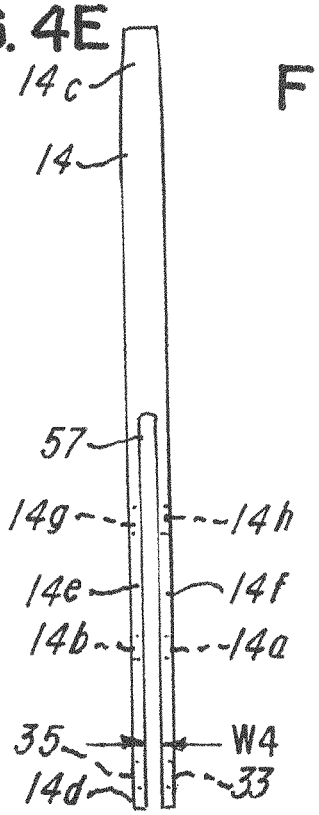

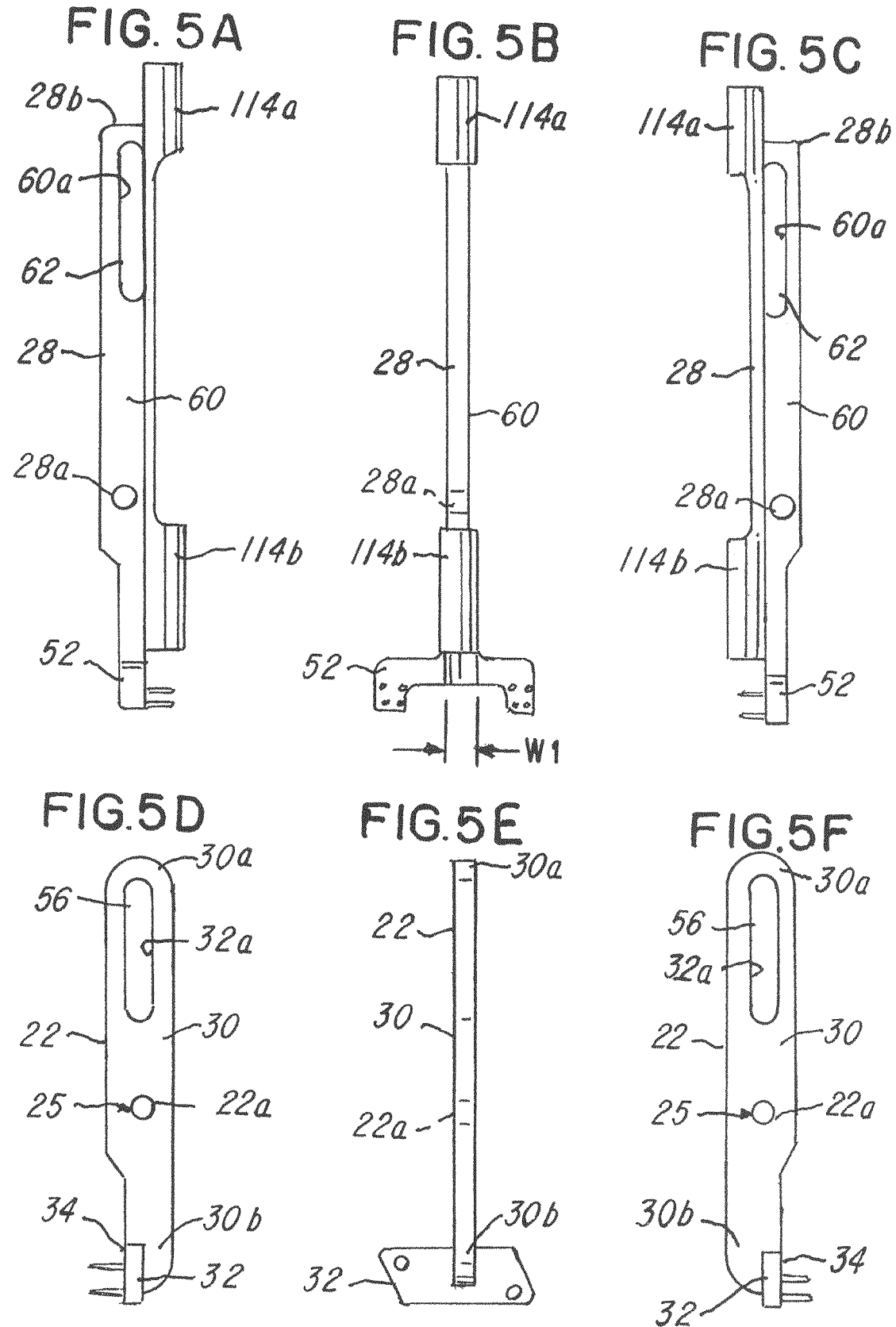

SURGICAL IMPLANT INSERTER COMPRESSOR

BACKGROUND OF THE INVENTION

1. Field of the Invention

This invention relates to a surgical tool, and more particularly, it relates to a surgical implant inserter compressor for implanting a surgical implant.

2. Background of the Invention

In the field of surgical implants, it is necessary to sometimes use a tool to hold the implant components when implanting and mounting them on bone, such as a cage that is mounted between vertebrae or plates that are mounted onto the spinous processes. For example, in some spinal surgeries, at least one or a plurality of plates are mounted or implanted on adjacent spinous processes to facilitate fusing, aligning or maintaining a relationship between these bones. One type of implant is shown and described in U.S. Patent Publication 2011/0172711, which is incorporated herein by reference and made a part hereof.

In the past, a typical tool for inserting these types of implants operated similar to a traditional pair of pliers in that the jaws of the tool pivoted about an axis and moved along an arcuate path when they opened and closed. One problem with using a tool of this type with the plates mentioned is that during mounting, any plates that were mounted on the jaws of the instrument did not engage the bone, such as the spinous processes, at substantially the same time or with the same amount of force. Unfortunately, this sometimes resulted in an uneven distribution of the forces with which the tool forced the plates into engagement with the spinous processes. This is especially true if the spinous processes were not of the same size or thickness or did not share a common longitudinal axis. This is illustrated in FIG. 8D. Notice that while the top spinous process SP1 shown in that figure is captured between the plates and if the surgeon desired to force the plates together until the bottom of the plates (as viewed in FIG. 8D) came into contact and engaged the lower spinous process in that figure, then the upper part of the plates shown in FIG. 8D would apply a greater force on the first spinous process SP1 than the force with which the lower part of the plate would apply to the second spinous process SP2. This could cause overstressing of the upper spinous process SP1. Alternatively, the lower part of one or both plates may not engage the spinous process at all in which case either one or both plates would not be locked, for example, to the lower spinous process SP2 as illustrated in FIG. 8D. This effect is referred to as "stress shielding", such as when the first spinous process SP1 shields the second spinous process SP2 from being engaged by at least one of the first or second plates in the illustration. Obviously, this can have undesired results, as the plate(s) not being locked into the first and second spinous processes SP1 and SP2.

What is needed, therefore, is a system and surgical implant inserter compressor that enables at least one or a plurality of surgical implants, such as plates, to engage the bones to which they are going to be affixed or mounted with a substantially common or equal amount of force and which distributes the clamping forces substantially evenly.

SUMMARY OF THE INVENTION

One object of the invention is to provide an improved surgical implant inserter compressor that applies at least one or a plurality of inserts onto bone with a substantially common or equal amount of force.

Another object of the invention is to provide a surgical implant inserter compressor that is adapted for use with at least one or a plurality of plates and that can drive the plates toward each other in a generally parallel relationship and/or along a common axis of movement.

Still another object of the invention is to provide a surgical implant inserter compressor that drives a pair of plates used to be mounted on adjacent spinous processes generally parallel and along a common axis movement so that a clamping force is generally distributed across the spinous processes or bone to which the implant is mounted.

Yet another object of the invention is to provide a surgical implant inserter compressor that has at least one jaw that is adapted to float or move about a pivot point or axis to accommodate differences in sizes, shapes, locations or the like, of bone.

Yet another object of the invention is to provide at least one or a plurality of guides in the surgical implant inserter compressor that is or are adapted to permit at least one or a plurality of jaws of the surgical implant inserter compressor to move along a common axis while maintaining a generally perpendicular relationship to that axis.

Another object of the invention is to provide a tool guide for guiding a tool into engagement with a fastener after the surgical implant has been clamped.

In one aspect, one embodiment comprises a surgical implant inserter for inserting a surgical implant comprising a first clamp, the first clamp having a first handle, a second clamp having a second handle pivotally coupled to the first handle at a fulcrum, at least one of the first clamp or the second clamp holding at least a portion of the surgical implant and a coupling for coupling the first and second handles to the first and second clamps such that they permit the first and second clamps to move toward and away from each other along a generally linear common axis of movement and permitting the first and second clamps to pivot or float when the first and second clamps drive the at least a portion of the surgical implant against at least one bone, thereby facilitating distributing a clamping force in response to an anatomy or shape of at least one bone to which the surgical implant is mounted.

In another aspect, another embodiment comprises a surgical implant inserter compressor, comprising a first pivot lever and a second pivot lever adjacently disposed relative to the first pivot lever and pivotally coupled thereto, the first pivot lever having a first clamp and the second pivot lever having a second clamp, the first and second clamps being pivotally coupled to the first lever and second lever, respectively, the first and second clamps being moveably secured to the second and first pivot levers, respectively, to permit the first and second clamps to move toward and away from each other along a clamping axis while remaining generally parallel with respect to each other.

These and other objects and advantages of the invention will be apparent from the following description, the accompanying drawings and the appended claims.

BRIEF DESCRIPTION OF THE DRAWINGS

FIG. 1 is a view of a surgical implant inserter compressor in open position in accordance with one embodiment;

FIG. 1A is a view illustrating various components of a spinous process implant that may be used with the surgical implant inserter compressor in accordance with one embodiment;

FIG. 2 is an exploded view of the surgical implant inserter compressor shown in FIG. 1;

FIG. 3A is view illustrating the surgical implant inserter compressor in a closed position wherein the plates of the implant shown in FIG. 1A are mounted on adjacent spinous processes SP1 and SP2;

FIG. 3B is an enlarged view of the implant mounted on the adjacent spinous processes;

FIG. 4A is a left-side view of a first handle;

FIG. 4B is a front view of the first handle shown in FIG. 4A;

FIG. 4C is right-side view of the first handle shown in FIG. 4B;

FIG. 4D is a left-side view of a second handle;

FIG. 4E is a front view of the second handle shown in FIG. 4D;

FIG. 4F is a right-side view of the second handle shown in FIG. 4E;

FIG. 5A is a left-side view of a second clamp in accordance with one embodiment;

FIG. 5B is a front view of the second clamp shown in FIG. 5A showing features of a second jaw;

FIG. 5C is a right-side view of the second clamp shown in FIG. 5B;

FIG. 5D is a left-side view of a first clamp in accordance with one embodiment;

FIG. 5E is a front view of the first clamp shown in FIG. 5D;

FIG. 5F is a right-side of the first clamp shown in FIG. 5E;

DETAILED DESCRIPTION OF PREFERRED EMBODIMENTS

Figure 6A:
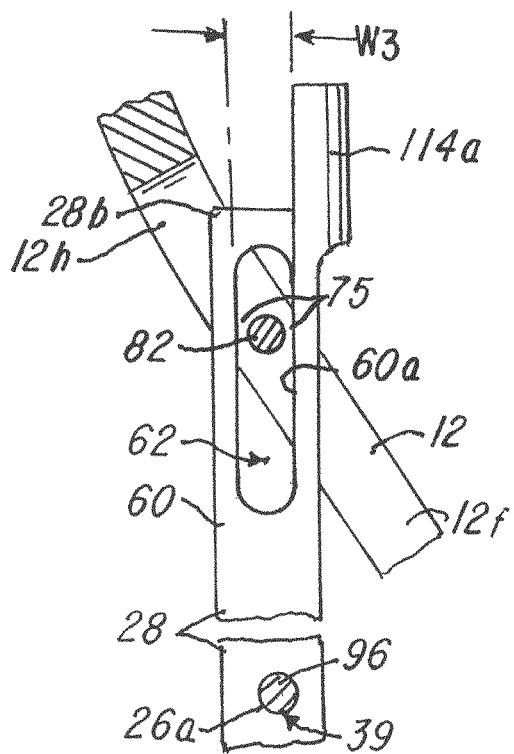
FIG. 6A is a fragmentary sectional view showing the relationship of various components that enable the second clamp, jaw and any associated plate mounted thereon being able to pivot or float so that it can accommodate different anatomical characteristics of the bone to which the plate is mounted.

Referring now to FIG. 1, a surgical implant inserter compressor 10 and system is shown. The surgical implant inserter compressor 10 comprises a first pivot lever or handle 12 and a second pivot lever or handle 14 that is pivotally coupled to the first pivot lever or handle 12 at a pivot joint 16 which defines a fulcrum. In one example, the pivot joint 16 comprises a fastener in the form of a pin 17 (FIG. 1) that is press-fit into apertures 19 and 21 (FIG. 2) defined by generally cylindrical walls 12a and 12b, respectively, in the first pivot lever or handle 12 and rotatably received in aperture 23 defined by the generally cylindrical walls 14a and 14b in the second pivot lever or handle 14.

In the illustration being described, the first pivot lever or handle 12 comprises a first or handle end 12c and a second or clamp end 12d. Likewise, the second pivot lever or handle 14 comprises a first or grip end 14c and a second or clamp end 14d. Notice that the second or clamp end 12d of the first pivot lever or handle 12 is generally U-shaped and comprises a first wall 12e and a generally opposed second wall 12f. In the illustration being described the first and second walls 12e, 12f cooperate to define an aperture or channel 18 for receiving various components as will be described later herein.

The first pivot lever or handle 12 is pivotally coupled to a first clamp 22 at a second pivot joint 20 (FIG. 1) using a fastener, such as a pivot pin 20a, that is press-fit into aperture 27 of generally circular and mating walls 29 and 31. The pivot pin 20a is also received in an aperture 25 defined by the cylindrical wall 22a. Details of the first clamp 22 will be described later herein.

Note that the second lever or handle 14 also comprises a generally U-shaped end 14d and has a first wall 14e and a generally opposed second wall 14f that cooperates with the first wall 14e to define a generally U-shaped channel 24. Note that the second pivot lever or handle 14 is also pivotally coupled at its second end 14d to a second clamp 28 at a third pivot joint 26 (FIG. 1) as shown. In this regard, a fastener or pivot pin 26a is received and press-fit in the aperture 39 defined by walls 33 and 35 in the second pivot lever or handle 14 to pivotally couple the second clamp 28 to the second pivot lever or handle 14. Thus, the pivot pin 26a is also received in aperture 39 (FIG. 2) defined by a second wall 28a in the second clamp 28, and the second clamp 28 is adapted to pivot thereabout.

In the illustration being described, the first clamp 22 comprises a generally elongated member or portion 30 having a first end 30a and a second end 30b. Note that at the second end 30b, the first clamp 22 comprises a generally planar jaw or first compression jaw 32 having a support surface 34 having at least one or a plurality of support projections or barbs 36 (FIG. 5D) that are adapted and dimensioned to receive and support at least a portion of an implant 40. In this regard, FIGS. 1A and 3B show one type of implant that may be used with the surgical implant inserter compressor 10 as described herein. The features of this implant 40 are shown and described in U.S. Patent Publication 2011/0172711, now issued as U.S. Pat. No. 8,262,607, which is incorporated herein by reference and made a part hereof. For purposes of illustration, it should be appreciated that the implant 40 in the illustration being described comprises a first plate 42, a generally opposed second plate 44, and a set screw 46 which is threadably received in a threaded opening 48 of the second plate 44. In the illustration being described, a bridge member 50 of the type shown and disclosed in the aforementioned application may be used in the manner described therein. Inasmuch as this surgical implant inserter compressor 10 is particularly adapted and suitable for use with the implant 40 as shown and described in that application, that implant is illustrated for ease of illustration of the operation and use of the surgical implant inserter compressor 10.

Returning now to FIGS. 1, 1A and 2, note that the at least one or a plurality of support projections or barbs 36 are received in generally mating apertures 42a (FIG. 1A) and 42b, respectively, in the first plate 42 and are press-fit therein to support the first plate 42 on the jaw 32.

The second pivot lever or handle 14 comprises the second clamp 28 having a second jaw 52 and at least one or a plurality of support projections or barbs 54 that are received in mating apertures 58 (FIG. 1A) of the second plate 44 to thereby support the second plate 44 on the second jaw or second compression jaw 52. In the illustration being described, the bridge member 50 is mounted on an axle, cross bar or projection 42c of the first plate 42 and is received in an aperture 49 (FIG. 1A) defined by a wall 44a of the second plate 44. In the illustration being described, the implant 40 is preferably mounted between a first spinous process SP1 (FIG. 3B) and a second spinous process SP2 (FIG. 3). The bridge member 50 and axle, cross bar or projection 42c are positioned in the aperture 49 and may extend therethrough when the first and second plates 42 and 44 are moved towards each other and toward the first and second spinous processes SP1 and SP2 until the first and second plates 42 and 44 engage the opposing surfaces of the first and second spinous processes SP1 and SP2. As described in the aforementioned application, the first plate 42 and the second plate 44 may have engaging surfaces 42d and 44c, respectively, that comprise at least one or a plurality of projections, barbs or serrations 36 to facilitate frictional engagement and fastening between the first and second plates 42 and 44 and the first and second spinous processes SP1 and SP2.

Referring to FIG. 2, notice that the first clamp 22 comprises the first generally elongated member or portion 30 having the first end 30a. The generally elongated member or portion 30 comprises an internal wall 32a that defines an elongated slot or guide 56. Note that the first end 30a is slidably received in the generally U-shaped channel 24 of the second pivot lever or handle 14. A fastener, such as a pin or fastener 55, is received in the aperture 57 defined by generally cylindrical walls 14g and 14h and generally elongated slot 56 so that the elongated member or portion 30 is captured between the first and second walls 14e and 14f. The elongated slot 56 provides or defines a guide to guide or cause the pin or fastener 55 to travel linearly in the slot 56 so that the second clamp 28 and elongated member 30 remain generally vertical (as viewed in FIG. 2) or perpendicular with respect to an axis CA (FIGS. 1, 1A and 8B) during actuation of the first and second pivot levers or handles 12 and 14.

The second clamp 28 also comprises a generally elongated member 60 that has an interior wall 60a that defines a second elongated slot 62 as shown. An end 28b is received in the aperture or channel 18 and a fastener 82, such as a pin, is received and press-fit in the apertures 12g and 12h of the first pivot lever or handle 12 and second elongated slot 62, thereby capturing the generally elongated member 60 between the first and second walls 14e and 14f. As with the first elongated slot 56, the second elongated slot 62 provides a guide that causes the elongated member 60 to remain in a generally vertical position (as viewed in the FIG. 1) or generally perpendicular to the axis CA of movement when the first and second pivot levers or handles 12 and 14 are actuated.

Advantageously, the elongated slots 56 and 62 facilitate maintaining the first and second elongated members or portions 30 and 60, respectively, in a generally parallel relationship during use. This, in turn, causes the first and second jaws 32 and 52 to remain generally parallel during actuation of the first pivot lever or handle 12 and second pivot lever or handle 14. It has been found that maintaining this parallel relationship facilitates maintaining the first and second plates 42 and 44 in a generally parallel relationship with respect to each other when they are implanted on the first and second spinous processes SP1 and SP2. As best illustrated in FIGS. 3A and 3B, note that the first and second plates 42 and 44 engage and become mounted on the opposing sides of the first and second spinous processes SP1 and SP2 without a substantially constant or substantially distributed amount of force on the and second spinous processes SP1 and SP2.

Figure 8A:
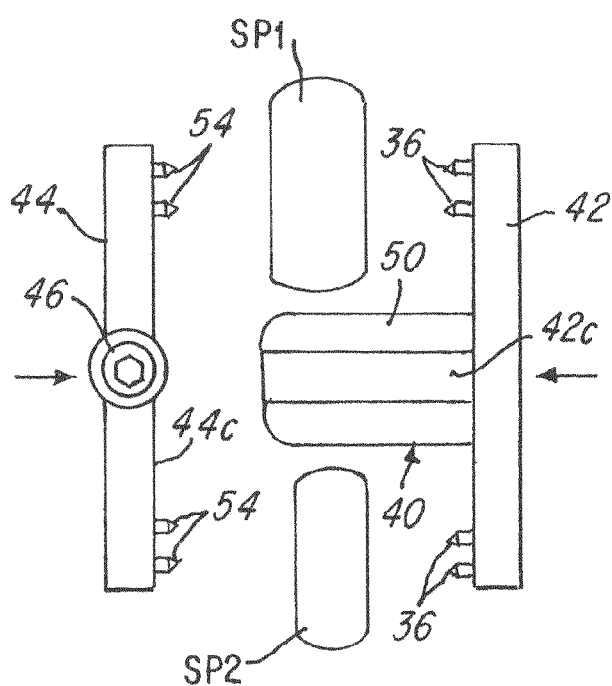
FIGS. 8A-8C are general simplified illustrations showing the pivoting and floating movement that is permitted by the surgical implant inserter compressor.
Figure 8B:
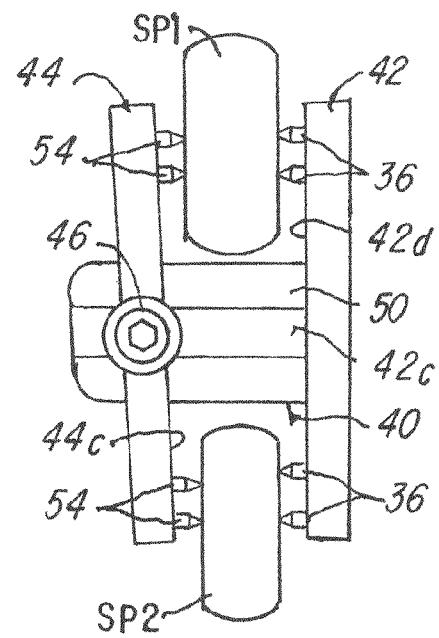
Figure 8C:
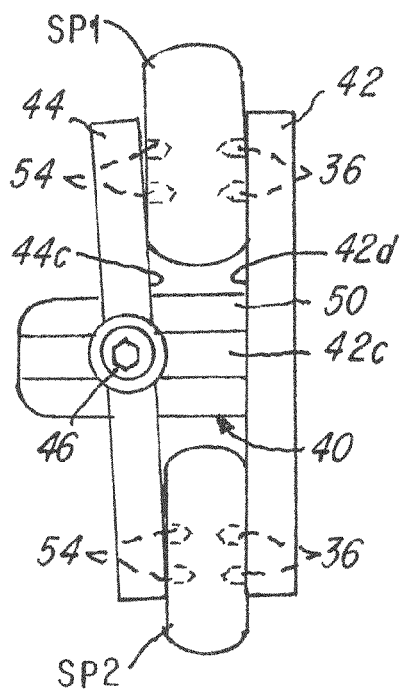

As illustrated in FIGS. 7A-7C and 8A-8C, it is not uncommon that the anatomical structure of the first and second spinous processes SP1 and SP2 is not identical, and oftentimes, these bones comprise different sizes, dimensions, shapes, alignment or anatomy. To illustrate this, note, for example, the first spinous process SP1 in FIGS. 8A and 8B is larger in width than the second spinous process SP2. It is important to account for the anatomical differences between the first and second spinous processes SP1 and SP2 so that the implant 40 remains firmly in place after implantation and generally parallel with respect to each other. Accordingly, in one embodiment of the invention, at least one or both of the first and second jaws 32 and 52 is adapted to "float" or move in response to the anatomical shape, dimension or size of the first and second spinous processes SP1 and SP2. In one embodiment, at least one or both of the first and second jaws 32 and 52 can float or move in order to distribute the force or load with which the first and second jaws 32 and 52 force the first and second plates 42 and 44 into engagement with the opposing surfaces of the first and second spinous processes SP1 and SP2. The effect of this feature is illustrated in FIGS. 8A-8C.

Note in FIG. 8A, that the first and second plates 42 and 44 are driven generally parallel to each other along a common axis CA (FIG. 1) and toward the first and second spinous processes SP1 and SP2. As the first and second plates 42 and 44 engage the first and second spinous processes SP1 and SP2 (FIG. 8B), note that the second plate 44 in the illustration is permitted to move or pivot into a non-parallel relationship, with respect to the first plate 42, so that the plurality of support projections or barbs 54 on the lower portion of the second plate 44 engage the second spinous process SP2 with a substantially equal amount of force with which the plurality of support projections or barbs 54 on the second plate 44 engage the first spinous process SP1. As the surgical implant inserter compressor 10 compresses and clamps the first and second plates 42 and 44 together (FIG. 8C), the plurality of support projections or barbs 59 (FIG. 1A) on the second plate 44 and the plurality of support projections or barbs 61 on the first plate 42 can be driven with substantially an equal amount of force into the first and second spinous processes SP1 and SP2 as shown in FIG. 8C.

Figure 8D:
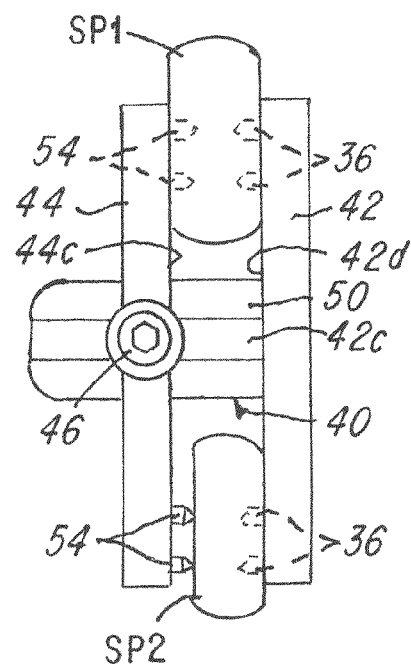
FIG. 8D is a view illustrating that, without the floating or pivoting movement enabled by the surgical implant inserter compressor, a stress shielding occurs and potential for the plates not to become locked or fixed onto bone as desired.

To illustrate the point further, FIG. 8D illustrates an example where the first and second plates 42 and 44 do not pivot and fail to engage the surfaces of the first and second spinous processes SP1 and SP2 with a substantially equal amount of force. Note in FIG. 8D that the larger first spinous process SP1 "shields" at least one or both surfaces of the second spinous process SP2 when the first and second plates 42 and 44 are implanted. Note that the lower plurality of support projections or barbs 59 on the second plate 44 are failing to engage the second spinous process SP2 with first and second plates 42 and 44 are mounted thereto. If engagement of the first and second plates 42 against the second spinous process SP2 is forced, then the plurality of support projections or barbs 59 at the upper part of the first and second plates 42 and 44 engage the first spinous process SP1 with greater force than the lower, which can over stress the upper portion of the first spinous process SP1.

Figure 6B:
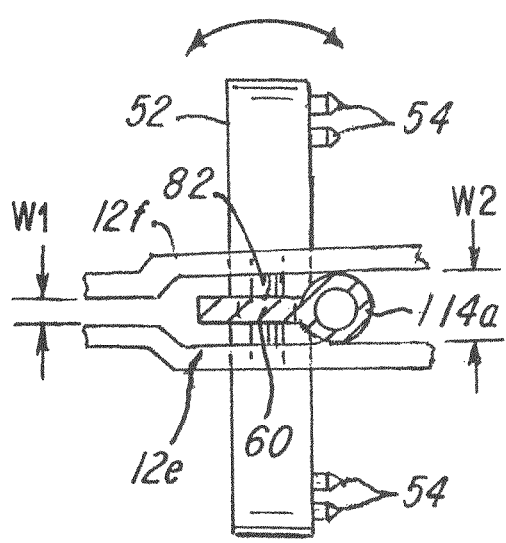
FIG. 6B is sectional plan view showing various features of the second clamp.
Figure 7A:
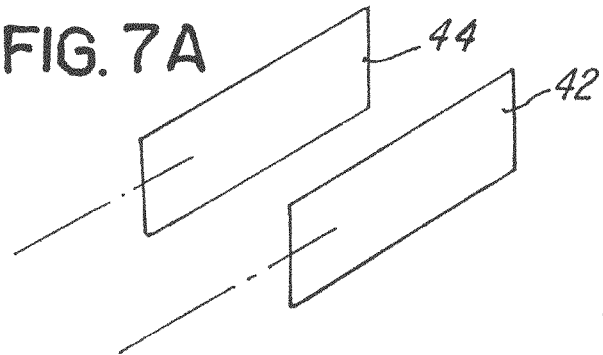
FIG. 7A-7C are various illustrative views showing various planes and the pivoting movement of the first and second jaws of the first and second clamps in order to accommodate the anatomical environment in which the implant plates are to be mounted.
Figure 7B:
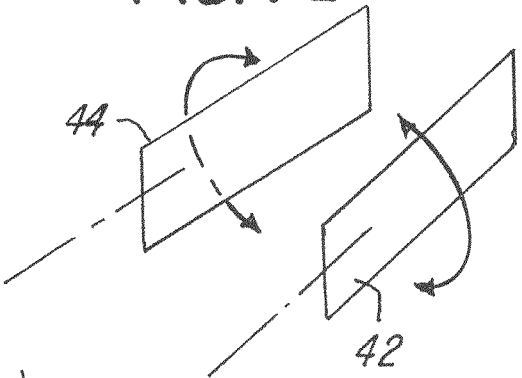
Figure 7C:
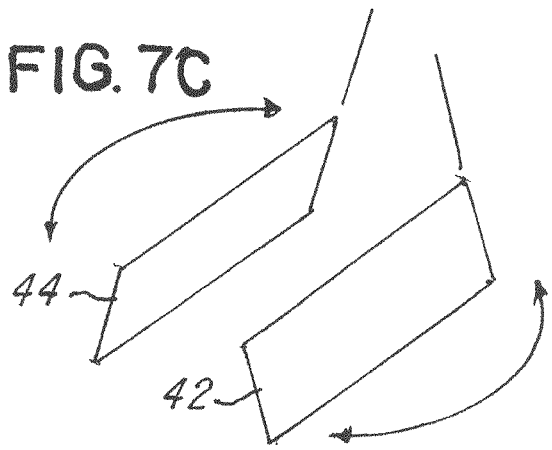

This problem of one bone "shielding" another is overcome in one embodiment because at least one of the first or second clamps 22 or 28 floats or moves, and this feature will now be described. For ease of description, the floating movement will be described with respect to the second clamp 28, but it should be understood that the first clamp 22 may also comprise the same floating pivotal movement as well. Advantageously, the floating or pivotal second clamp 28 is adapted to permit the jaw 52 to pivot in the direction of double arrows A and B (FIGS. 1 and 7B) so that the second plate 44 can pivot or move with respect to the clamping axis CA (FIG. 1) and about a longitudinal axis of the elongated member 60. This facilitates the first and second plates 42 and 44 adapting to the anatomy of the bones to which they are mounted and or facilitate distributing the clamping force during compression of the first and second plates 42 and 44 against the first and second spinous processes SP1 and SP2. To provide or facilitate this pivotal toggle or floating movement of the jaw 52, a width W1 (FIG. 5B) of the elongated member 60 is smaller than the width W2 (FIG. 4B) at an elongated area 80 (FIG. 4B) between the inner surfaces 12e1 and 12f2 of the first and second walls 12e and 12f, respectively. Note also that a dimension or diameter of the fastener 82 (FIG. 2) is smaller than a width W3 (FIG. 6A) which provides space or leeway 75 between the pin or fastener 82 (FIG. 2) and the wall 60a. Likewise, a diameter of the second wall 28a is slightly larger than a diameter of pivot pin 26a, both of which enable or facilitate the elongated member 60 to toggle or pivot about its longitudinal axis as shown in FIG. 6B, thereby enabling the jaw 52 and the second plate 44 to also toggle or pivot in the direction of double arrow A (FIG. 1A). Although not shown, it should be understood that one or more of the pivot joints and couplings between the first pivot lever or handle 12 and the first clamp 22 could be adapted to provide the same pivoting or "play", so the first clamp 22 could be adapted to float in response to the local anatomy.

Advantageously, this floating, pivoting or "play' enables the surgical implant inserter compressor 10 to accommodate or adjust to the anatomical differences between bones, such as differences in size, position, alignment, shape or dimension, of the first and second spinous processes SP1 and SP2.

Further details of the first and second pivot levers or handles 12 and 14 and first and second clamp 22 and 28 are shown in FIGS. 4A-4F and 5A-5F. Referring now to FIGS. 4A-4C, the first pivot lever or handle 12 comprises the second or clamp end 12d having the first wall 12e and generally opposing second wall 12f. As mentioned earlier herein, the first and second walls 12e and 12f cooperate to define the aperture or channel 18 in which the second pivot lever or handle 14 and the second first end 28b of the clamp 28 is received. To facilitate such accommodation, the first and second walls 12e and 12f have the generally elongated or U-shaped area 80 (FIG. 4B) so that it can accommodate and receive the second pivot lever or handle 14 as shown. The width W2 of the first pivot lever or handle 12 at the elongated area 80 is slightly larger than the width W4 (FIG. 4B) between the first and second walls 14e and 14f of the second pivot lever or handle 14.

In the illustration being described, note that a width W5 (FIG. 5E) of the generally elongated member or portion 30 is slightly smaller than a width W6 (FIG. 4B) between the surfaces 12e1 and 12f1 is substantially the same as width W6 (FIG. 6) so that the generally elongated member or portion 30 is guidably received and supported between the first and second pivot levers or handles 12 and 14 as shown.

During use, the first pivot lever or handle 12 and second pivot lever or handle 14 are moved to the open position, illustrated in FIG. 1, and the first and second plates 42 and 44 are detachably mounted onto the jaws 32 and 52, respectively. As the first and second pivot levers or handles 12 and 14 are actuated toward each other, this causes the jaws 32 and 52 and the first and second plates 42 and 44, respectively, mounted thereon to move toward each other while maintaining a generally parallel relationship and close toward the first and second spinous processes SP1 and SP2 to which they will be mounted.

Note that the jaws 32 and 52 remain generally parallel during such movement and lie in planes that remain generally perpendicular to the axis CA of movement. This movement should be contrasted to the movement of prior art tools (not shown) which typically caused the plates to move in an arc or along an arcuate path, which can cause an undesired uneven distribution of force when the implants engage the first and second spinous processes SP1 and SP2.

Gripping and actuating the first and second pivot levers or handles 12 and 14 is continued until the first and second plates 42 and 44 engage and are mounted on the first and second spinous processes SP1 and SP2 as shown in FIGS. 3A, 3B and 8A-8C. In the example described, the set screw 46 (FIGS. 1 and 1A) must be screwed and set to secure the first and second plates 42 and 44 together.

To facilitate retaining the surgical implant inserter compressor 10 in the locked and clamped position during screwing of the set screw 46, the surgical implant inserter compressor 10 comprises a lock 100. In the embodiment being described, the lock 100 is a threaded member 102 having a first end 104 pivotally secured to the first pivot lever or handle 12 and a second end 106 which freely pivots about a pin axis of a pivot pin 101.

The member 102 comprises an internal generally U-shaped wall 108 that defines a channel 110 for receiving the first end 14c of the second pivot lever or handle 14. Note that the member 102 has a threaded outer surface that receives a female threaded member 112. After the threaded member is "swung" over the first or grip end 14c so that the first or grip end 14c is received in the channel 110 when the surgical implant inserter compressor 10 is in the fully clamped position, the female threaded member 112 may be threadably tightened to retain the first and second pivot levers or handles 12 and 14 in the locked position as best illustrated in FIG. 3A. A stay 103 may also be provided to support the member 102 as shown.

To facilitate using tools, such as a screwdriver SD (FIG. 3A), with the surgical implant inserter compressor 10, the surgical implant inserter compressor 10 may comprise at least one or a plurality of tool guides 114 for guiding the tool into driving engagement with set screw 46 so that it can be screwed and tightened in order to lock the second plate 44 to the first plate 42. In the example, an upper tool guide 114a and lower tool guide 114b are coupled to or integrally formed with the elongated member 60. The tool guides 114a and 114b are generally cylindrical and define guide apertures 114a1 and 114c1 for guiding the tool SD into engagement with the set screw 46. It should be understood that more or fewer guides could be provided. Also, they could be situated on other parts or components of the surgical implant inserter compressor 10, such as on the elongated member or portion 30.

Unlike conventional implant inserters, the surgical implant inserter compressor 10 of the embodiment being described enables the jaws 32 and 52 to move along a common axis CA and generally parallel to each other, thereby enabling the first and second jaws 32 and 52 associated with the first and second plates 42 and 44, respectively, to move parallel to each other when they are moved into engagement with the first and second spinous processes SP1 and SP2. Thus, note when a distance D1 (FIGS. 1 and 3A) between the pivot joint 20 and the pin or fastener 55 increases from, for example, the position shown in FIG. 1 to the fully locked and clamped position shown in FIG. 3A, the distance D1 between the pivot joint 20 and the pin or fastener 55 increases, which is permitted by the movement of the pin or fastener 55 in the elongated slot 56 in the generally elongated member or portion 30 and the movement of pin or fastener 82 in the elongated slot 62 of the elongated member 60. Thus, the distance between the pivot joint 26 and the fastener 82 also increases as the jaws 32 and 52 are tightened. As mentioned, one or a plurality of jaws 32 and 52 may be adapted to pivot or float to accommodate the local anatomy and facilitate distributing compressive forces.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A surgical implant inserter compressor for use with a surgical implant comprising at least a first plate and a second plate comprising:
    a first clamp having a first handle;
    a second clamp having a second handle pivotally coupled to said first handle at a fulcrum, at least one of said first clamp or said second clamp for holding at least a portion of said surgical implant; and
    a coupling for coupling said first and second handles to said first and second clamps such that said coupling permits said first and second clamps to move toward and away from each other along a generally linear common axis of movement and permits said first and second clamps to pivot or float when said first and second clamps drive said at least a portion of said surgical implant against at least one bone, thereby facilitating a distribution of a clamping force in response to an anatomy or shape of at least one bone to which said surgical implant is mounted;
    said first clamp comprising a first elongated member and a first clamp jaw and said second clamp comprising a second elongated member and a second clamp jaw;
    said first and second clamp jaws being adapted to receive and support said first plate and said second plate, respectively;
    said coupling being adapted to permit said first and second clamp jaws to move generally parallel toward each other when said first and second handles are actuated;
    wherein said coupling is also adapted to permit at least one of said first clamp jaw or said second clamp jaw to pivot with respect to said common axis prior to said first and second plates being mounted thereon and also in response to said first and second plates engaging at least one of a first spinous process or a second spinous process;
    said first and second clamp jaws lying in a first plane and a second plane, respectively, that are generally parallel to each other and generally perpendicular to said generally linear common axis of movement when said first and second clamp jaws move towards and away from each other;
    wherein said first elongated member has a first elongated slot and said second elongated member has a second elongated slot, said first handle having an end pivotally coupled at a first pivot joint to said first elongated member and said second handle having an end pivotally coupled at a second pivot joint to said second elongated member;
    said coupling comprises a first coupler or fastener for securing to said first handle, said first coupler or fastener captured in said second elongated slot of said second elongated member, and a second coupler or fastener for securing to said second handle, said second coupler or fastener captured in said first elongated slot of said first elongated member, wherein said first and second couplers or fasteners cooperating with said first and second elongated slots to cause said first and second jaw members to remain generally parallel during clamping.

2. The surgical implant inserter compressor as recited in claim 1 wherein each of said first and second handles have a gripping end and a second end generally opposite said gripping end, said first and second handles having a generally U-shaped first elongated portion and a generally U-shaped second elongated portion, respectively, defining a first elongated opening and a second elongated opening, respectively;
    said first elongated opening of said first handle being adapted to receive said first elongated member of said first clamp and said second elongated opening of said second handle being adapted to receive said second elongated member of said second clamp;
    said coupling further comprising a first pivotal coupling for coupling said second end of said first handle to said first elongated portion and a second pivotal coupling for coupling said second end of said second handle to said second elongated portion;
    said first and second couplers or fasteners, said first and second elongated slots, and said first and second pivotal couplings being adapted and dimensioned to permit at least one of said first end or said second end to pivot or float to accommodate a local anatomy that includes a first spinous process and a second spinous process.

3. The surgical implant inserter compressor as recited in claim 1 wherein said first pivot joint, said first coupler and said first elongated slot are sized and adapted to permit said first clamp jaw to pivot or float relative to said axis of movement.

4. The surgical implant inserter compressor as recited in claim 3 wherein said second pivot joint, said second coupler and said second elongated slot are sized and adapted to permit said second clamp jaw to pivot relative to said axis of movement.

5. The surgical implant inserter compressor as recited in claim 1 wherein at least one of said first plate or said second plate having a fastener for coupling said first and second plates together;
    at least one of said first elongated member or said second elongated member having a tool guide for guiding a tool for actuating said fastener to lock said first and second plates together.

6. The surgical implant inserter compressor as recited in claim 1 wherein said end of said first handle has a first wall and a second wall generally opposing said first wall and defining a generally U-shaped captures both said second handle and said first elongated member.

7. The surgical implant inserter compressor as recited in claim 1, wherein the inserter compress further comprising a screw driver guide.

8. The surgical implant inserter compressor as recited in claim 1 wherein said first and second clamp jaws are of different shapes.

9. The surgical implant inserter compressor as recited in claim 8 wherein at least one of said first or second clamp jaws being generally U-shaped and the other being generally planar.

10. The surgical implant inserter compressor as recited in claim 1 wherein said surgical implant inserter compressor comprises a lock for locking said first and second clamps in a locked position.

11. The surgical implant inserter compressor as recited in claim 10 wherein said lock comprises a generally U-shaped threaded member pivotally coupled to one of said first handle or said second handle and having a slot or area for receiving the other of said second handle or said first handle, respectively, and a threaded female member for threadably mounting on said generally U-shaped threaded member and for locking said first and second handles together.

12. The surgical implant inserter compressor as recited in claim 1 wherein said first clamp and said second clamp are coupled together at a plurality of locations, each coupling being adapted to provide some pivoting movement or play so that said first and second clamps can float or pivot.

* * * * *